(12) United States Patent
Wang et al.

(10) Patent No.: US 12,409,251 B2
(45) Date of Patent: Sep. 9, 2025

(54) TISSUE-DERIVED SCAFFOLDING MATERIALS AND METHOD FOR TISSUE FORMATION

(71) Applicant: The Trustees of The Stevens Institute of Technology, Hoboken, NJ (US)

(72) Inventors: Hongjun Wang, Millburn, NJ (US); Meng Xu, Secaucus, NJ (US); Deep Parikh, South Plainfield, NJ (US); Jin Zou, Rutherford, NJ (US); Weiwei Wang, Jersey City, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 210 days.

(21) Appl. No.: 18/117,320

(22) Filed: Mar. 3, 2023

(65) Prior Publication Data

US 2023/0302199 A1 Sep. 28, 2023

Related U.S. Application Data

(62) Division of application No. 15/885,408, filed on Jan. 31, 2018, now Pat. No. 11,612,676.

(60) Provisional application No. 62/452,747, filed on Jan. 31, 2017.

(51) Int. Cl.

| A61L 27/36 | (2006.01) |
| A61L 27/18 | (2006.01) |
| A61L 27/52 | (2006.01) |
| A61L 27/54 | (2006.01) |
| A61L 27/56 | (2006.01) |
| A61L 27/58 | (2006.01) |
| A61L 27/60 | (2006.01) |
| C12N 5/00 | (2006.01) |
| G01N 33/50 | (2006.01) |

(52) U.S. Cl.
CPC ........... *A61L 27/3691* (2013.01); *A61L 27/18* (2013.01); *A61L 27/3604* (2013.01); *A61L 27/3608* (2013.01); *A61L 27/365* (2013.01); *A61L 27/3666* (2013.01); *A61L 27/52* (2013.01); *A61L 27/54* (2013.01); *A61L 27/56* (2013.01); *A61L 27/58* (2013.01); *A61L 27/60* (2013.01); *C12N 5/0062* (2013.01); *C12N 5/0075* (2013.01); *G01N 33/5011* (2013.01); *G01N 33/5082* (2013.01); *A61L 2430/02* (2013.01); *A61L 2430/28* (2013.01); *C12N 2500/84* (2013.01); *C12N 2503/02* (2013.01); *C12N 2513/00* (2013.01); *C12N 2533/00* (2013.01); *C12N 2533/30* (2013.01); *C12N 2533/74* (2013.01); *C12N 2539/00* (2013.01)

(58) Field of Classification Search
None
See application file for complete search history.

(56) References Cited

U.S. PATENT DOCUMENTS

2006/0216321 A1* 9/2006 Lyu .................. A61L 27/56
                                                        424/422
2010/0267143 A1* 10/2010 Park ................ C12N 5/0068
                                                        435/402

* cited by examiner

*Primary Examiner* — Nghi V Nguyen
(74) *Attorney, Agent, or Firm* — Clark Hill PLC; Ralph W. Selitto; John K. Kim

(57) ABSTRACT

In accordance with the method of the present invention, 3D tissue-derived scaffolding materials are made in various formats, including but not limited to hydrogel, sponge, fibers, microspheres, and films, all of which function to better preserve natural extracellular matrix molecules and to mimic the natural tissue environment, thereby effectively guiding tissue regeneration. The method involves incorporating a homogenized tissue-derived suspension into a polymeric solution of synthetic, natural, or hybrid polymers to prepare tissue-derived scaffolds in the aforementioned formats. Such tissue-derived scaffolds and scaffolding materials have a variety of utilities, including: the creation of 3D tissue models such as skin, bone, liver, pancreas, lung, and so on; facilitation of studies on cell-matrix interactions; and the fabrication of implantable scaffolding materials for guided tissue formation in vivo. The tissue-derived scaffolds and scaffolding materials made in accordance with the present invention also provide the opportunity to correlate the functions of extracellular matrix with tissue regeneration and cancer metastasis, for example.

17 Claims, 12 Drawing Sheets

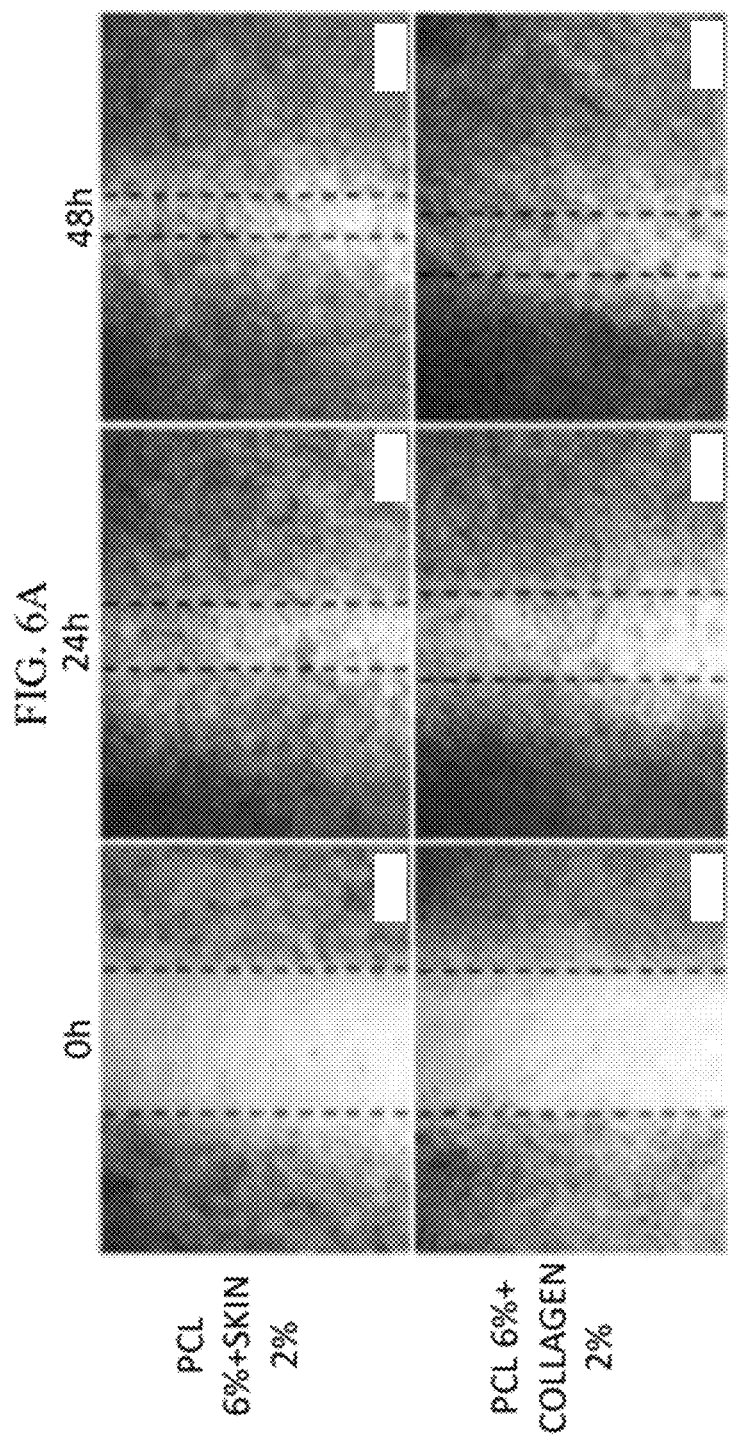

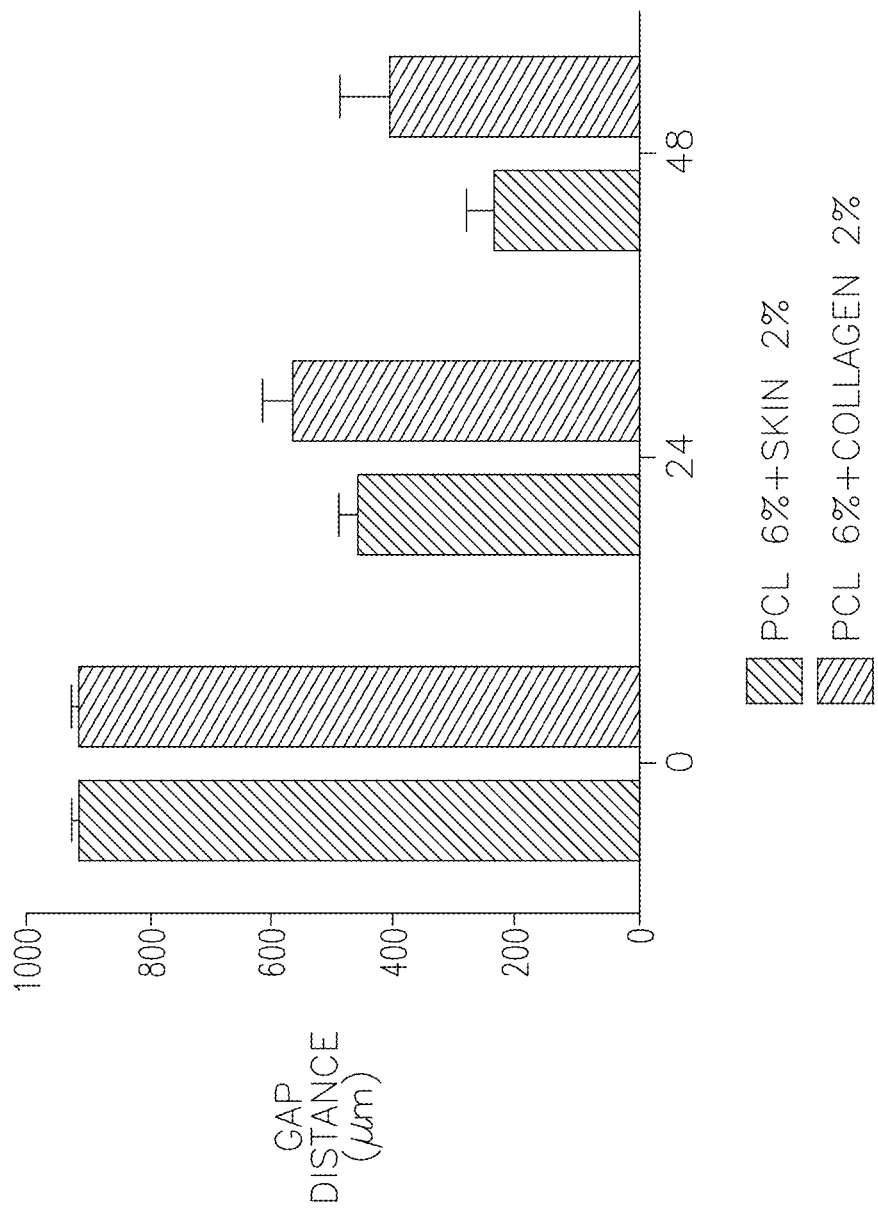

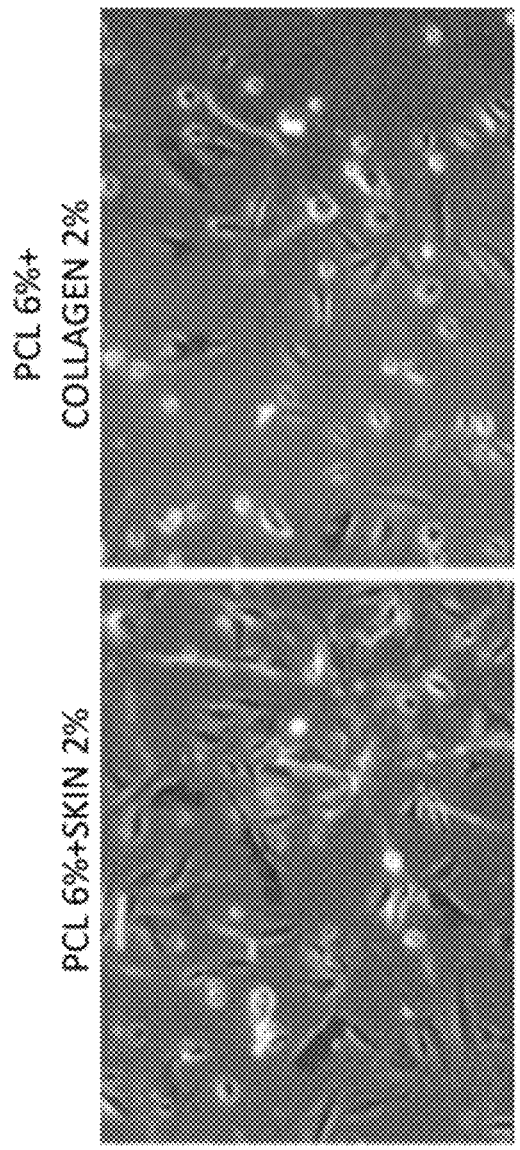

TISSUE-DERIVED SCAFFOLDING MATERIALS AND METHOD FOR TISSUE FORMATION

CROSS-REFERENCE TO RELATED APPLICATIONS

The present application claims the benefit of U.S. Provisional Application No. 62/452,747, filed Jan. 31, 2017 and entitled TISSUE-DERIVED SCAFFOLDING MATERIALS FOR TISSUE FORMATION, which provisional application, including its specification, abstract and drawings, is incorporated herein by reference in its entirety.

FIELD OF INVENTION

The present invention relates to biomedical engineering, and more particularly, to tissue regeneration using three-dimensional scaffolds.

BACKGROUND

A variety of three-dimensional (3D) scaffolds have been developed and used for in vitro creation of tissues and tissue models or for in vivo repair and regeneration of dysfunctional or damaged tissues in the attempt to facilitate and guide tissue formation. During tissue formation, the use of 3D scaffolds provides the cells with a temporary platform to attach, migrate, and proliferate. It also defines an influential microenvironment to regulate the cellular responses and subsequently affects the synthesis of new tissue matrix for various functions. Ideally, the 3D scaffolds should maximally replicate the natural growing environment of the cells to induce desirable cell phenotype expression and tissue matrix synthesis. However, as a result of the limitations of the fabrication technology and the limited available knowledge of the natural cell growing environment, minimal progress has been made towards the development of biomimetic 3D scaffolds. As a consequence, allogenic and autogenic grafts still dominate the efforts in scaffold-guided tissue regeneration. While such grafts certainly have advantages in promoting tissue repair and regeneration, their limited availability, large batch-to-batch variation, high risk for disease transmission, and mismatched physicochemical properties, may significantly hinder their further application.

In recognition of the essential biological functions of natural tissue matrix, extensive efforts have been made to incorporate some matrix-related molecules such as collagen, glycosaminoglycans, fibrinogen, laminin and fibronectin, whether individually or in combination, into 3D scaffolds. Considering the compositional and structural complexity of native tissue matrix from tissue to tissue, simple incorporation of such molecules in the 3D scaffolds cannot fully recapture the uniqueness of each tissue matrix. In this regard, it is highly desirable for 3D scaffolds to effectively recapture the key attributes of individual extracellular matrix ("ECM") of native tissues, like skin, bone, cartilage, cardiac, intestine, cornea, lung, kidney, nerve, and so on, respectively.

SUMMARY

The present invention relates to new and improved 3D scaffolding materials and methods for making same. The inventive 3D scaffolding materials, which can recapture the key physicochemical properties of native organ/tissue, are obtained by combining the solute of targeted tissues or cultured tissue from various cells with other materials (such as synthetic, natural, or a hybrid of both) to form various formats, such as fibers, particles, sponges, films, membranes and hydrogels. This novel combination not only allows the tuning of the physicochemical properties, such as mechanical properties like degradation rate, gelation time, and structural and morphological stability, but also minimizes the amount of tissue needed for fabrication of a large quantity of 3D scaffolding materials. The present invention effectively minimizes the challenges associated with decellularized tissue matrix, such as hard-to-infiltrate cells and large batch-to-batch variation, by providing new scaffolding materials which maintain a composition similar to a natural extracellular matrix, and which can be produced at a relatively low cost and in different formats.

With 3D scaffolding materials made in accordance with the present invention, it becomes possible to customize the unique microenvironment for individual tissue cells to better maintain their phenotype for functional tissue formation in vivo upon insertion into defected sites. Moreover, the tissues created in vitro with such 3D scaffolds could be used as models for drug evaluation or tools for fundamental studies such as cancer metastasis. Furthermore, the tissues created in vitro can also be implanted into the traumatic sites to fully or partially restore bodily functions. Such tissue-derived 3D scaffolding materials also provide for more personalized medicine as they enable the manufacture of implants that have a minimal number of immune responses since the tissue-derived 3D scaffolds use the patient's own tissue or tissues formed from a patient's own cells. Tissue-derived 3D scaffolding materials also serve as the important substrate for studying cell-cell and cell-matrix interactions within physiologically relevant microenvironments similar to native settings, thereby enabling a better understanding of cellular mechanisms and eventually leading to better therapeutic developments.

BRIEF DESCRIPTION OF THE DRAWINGS

For a more complete understanding of the present invention, reference is made to the following detailed description of an embodiment considered in conjunction with the accompanying drawings, in which:

FIGS. 5A-5E are various photographs and graphs showing the characterization of porcine skin-derived fibrous matrices, wherein pure collagen was used as a control in addition to polycaprolactone (PCL) fibers;

FIGS. 6A and 6B depict skin derived fibrous matrices promoting the migration of human dermal fibroblasts with wound healing;

FIGS. 6C-6E depict skin derived fibrous matrices promoting the migration of human dermal fibroblasts with time-lapse microscopy, with or without the presence of transforming growth factor (TGF)-β1.

DETAILED DESCRIPTION OF THE EXEMPLARY EMBODIMENT

Figure 1:
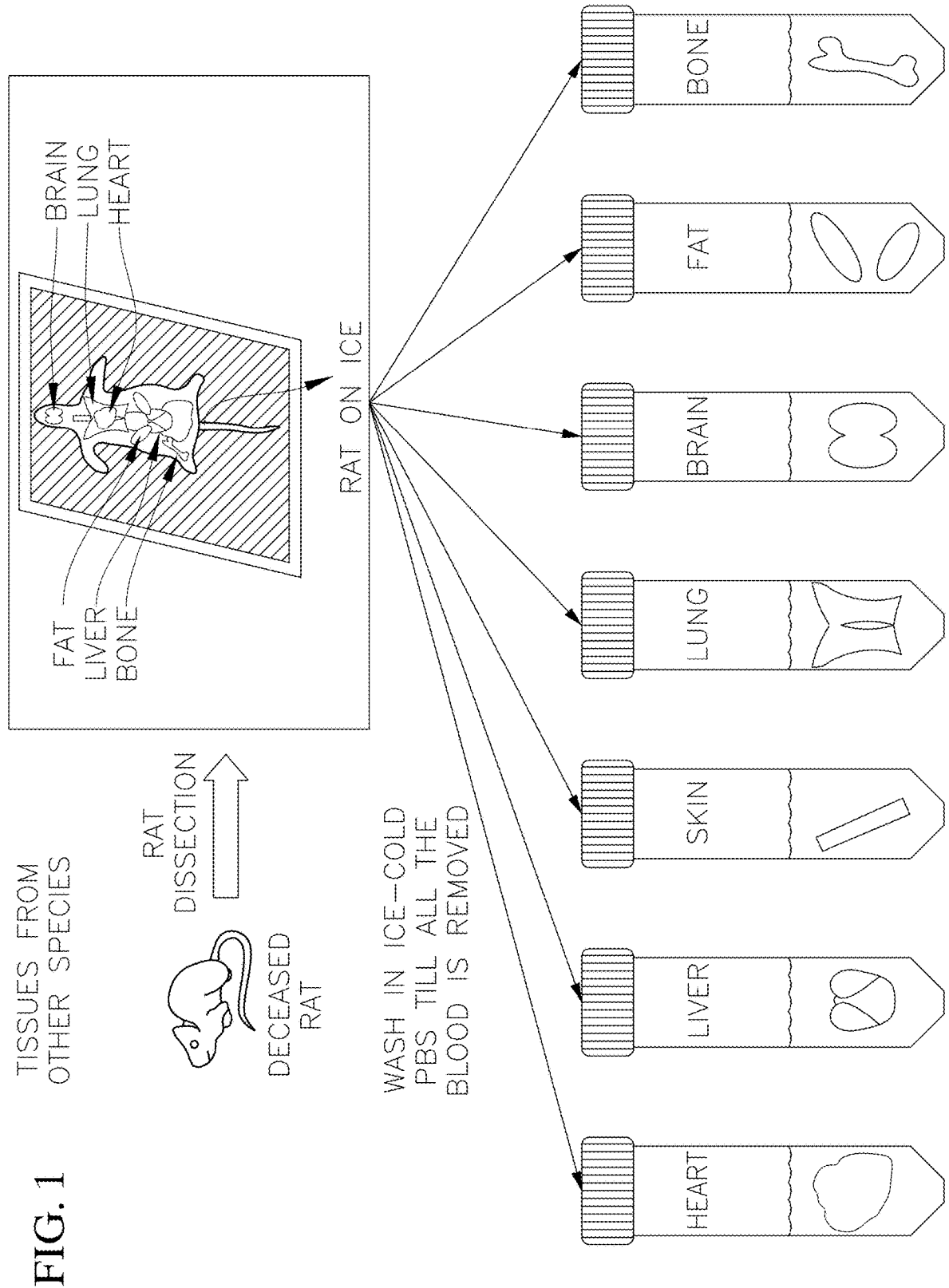
FIG. 1 is a schematic showing the collection of various tissues from other species or engineered tissues from cells.
Figure 2:
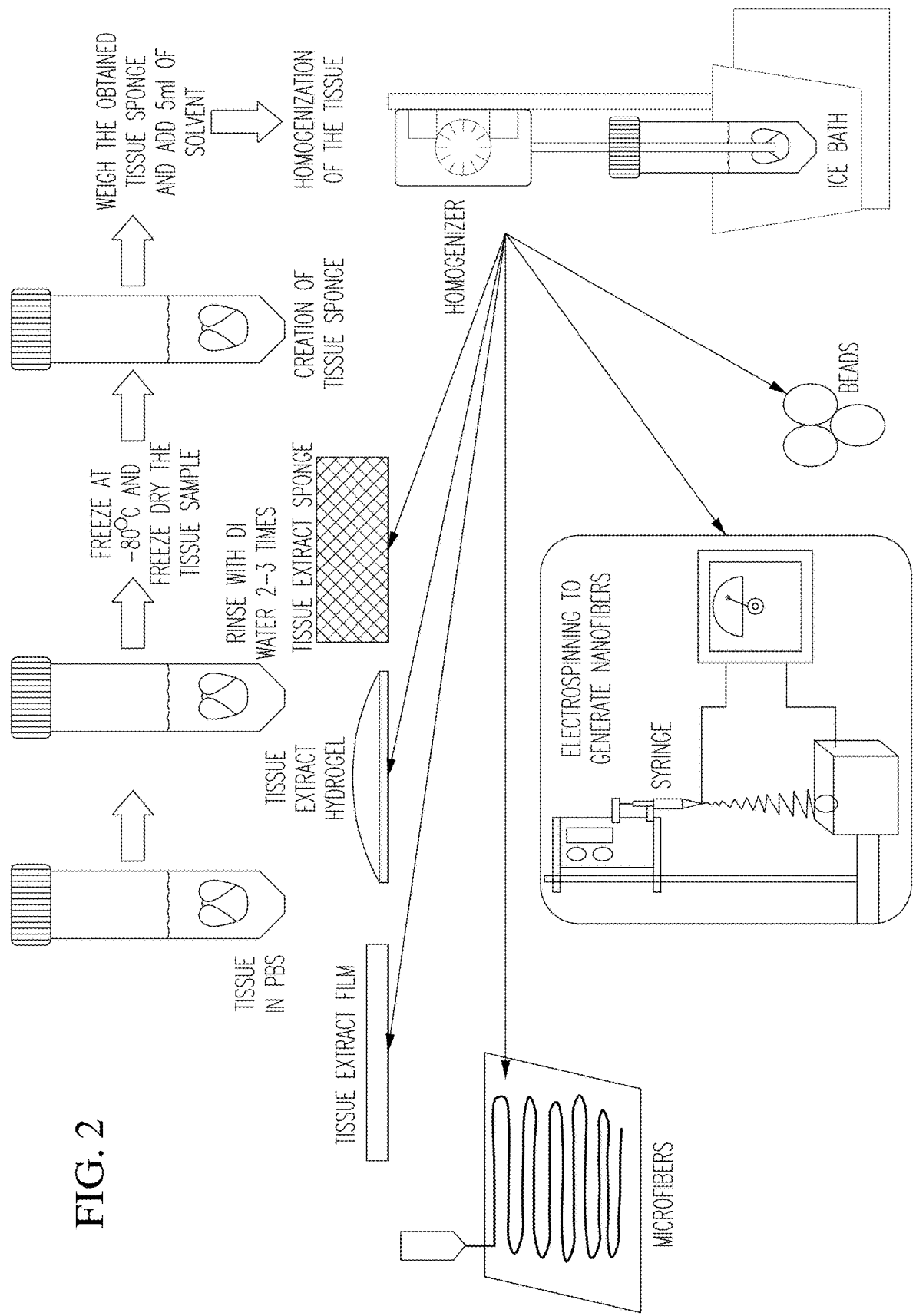
FIG. 2 is a schematic showing the typical procedure for processing tissues for fabricating various tissue-derived scaffolding materials.
Figure 3:
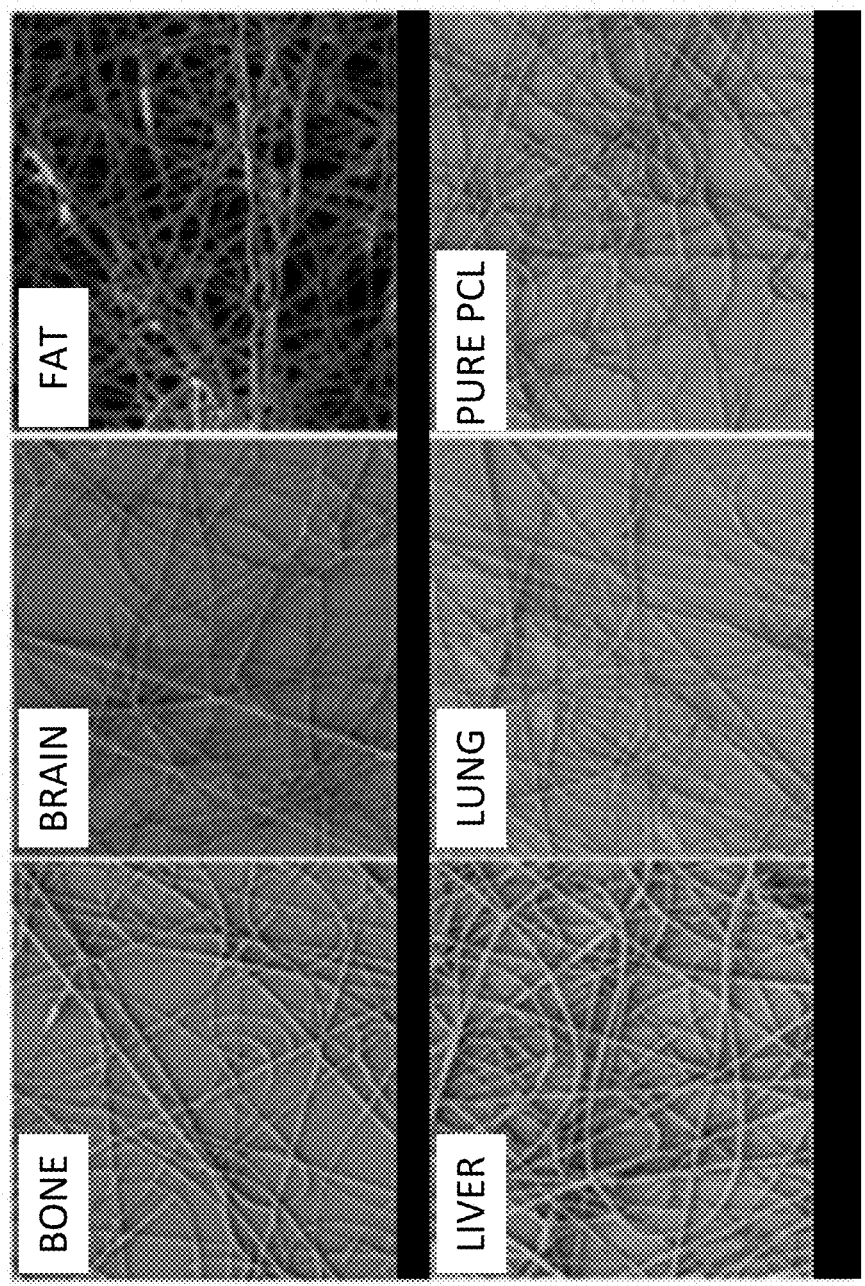
FIG. 3 is a set of six representative scanning electron microscopic micrographs of tissue-derived fiber matrices.
Figure 4:
FIG. 4 is a collection of six graphs showing the proliferation of breast cancer cells on various tissue-derived fibrous matrices.
Figure 5A:
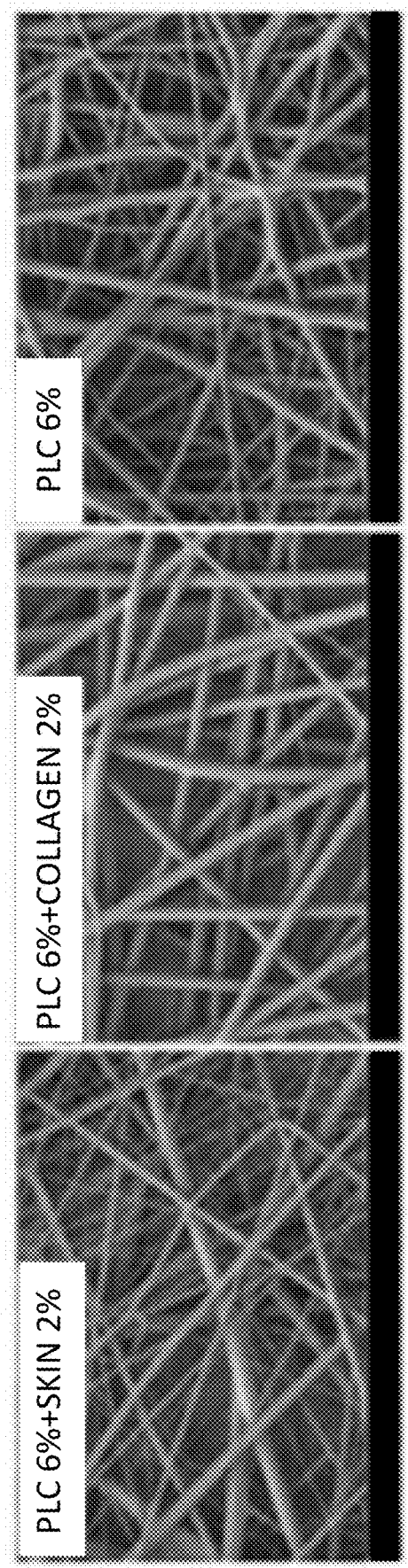
Figure 5D:
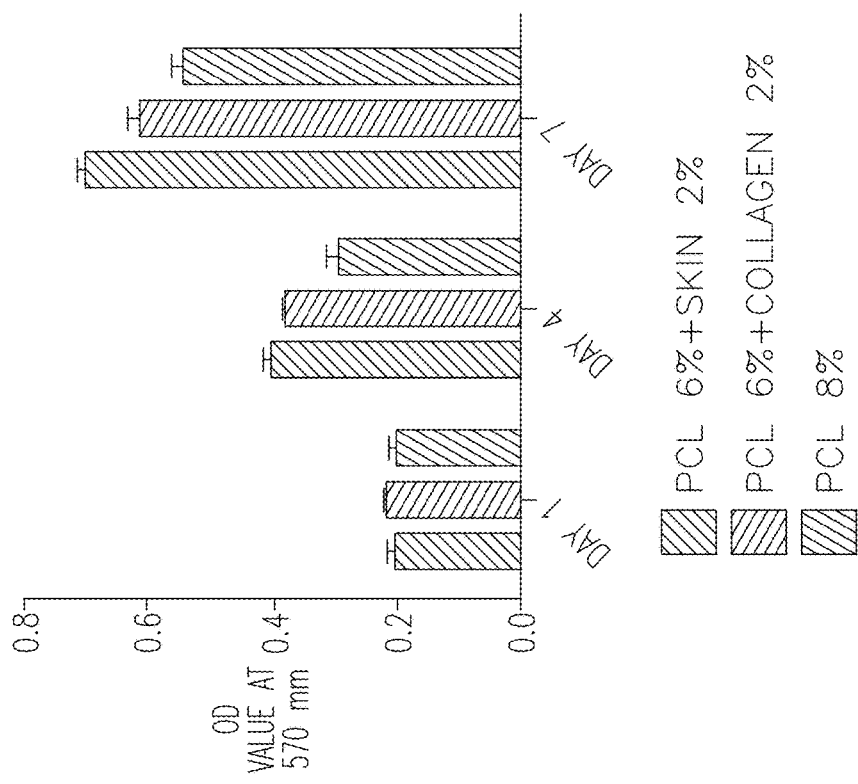
Figure 5B:
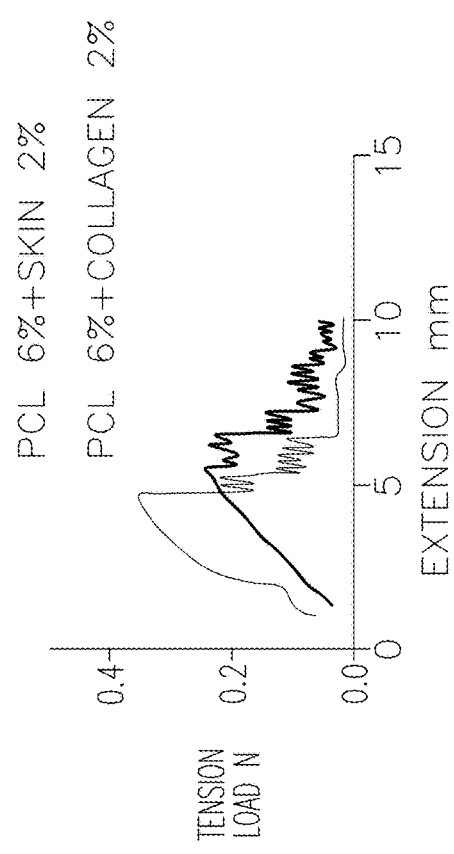
Figure 5C:
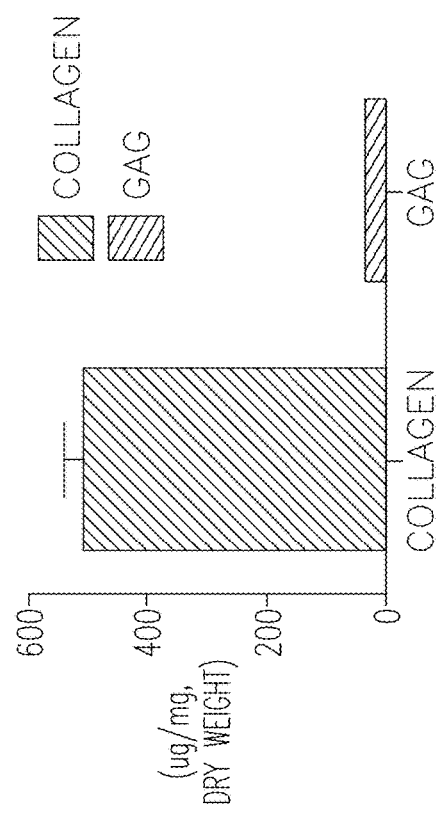
Figure 6D:
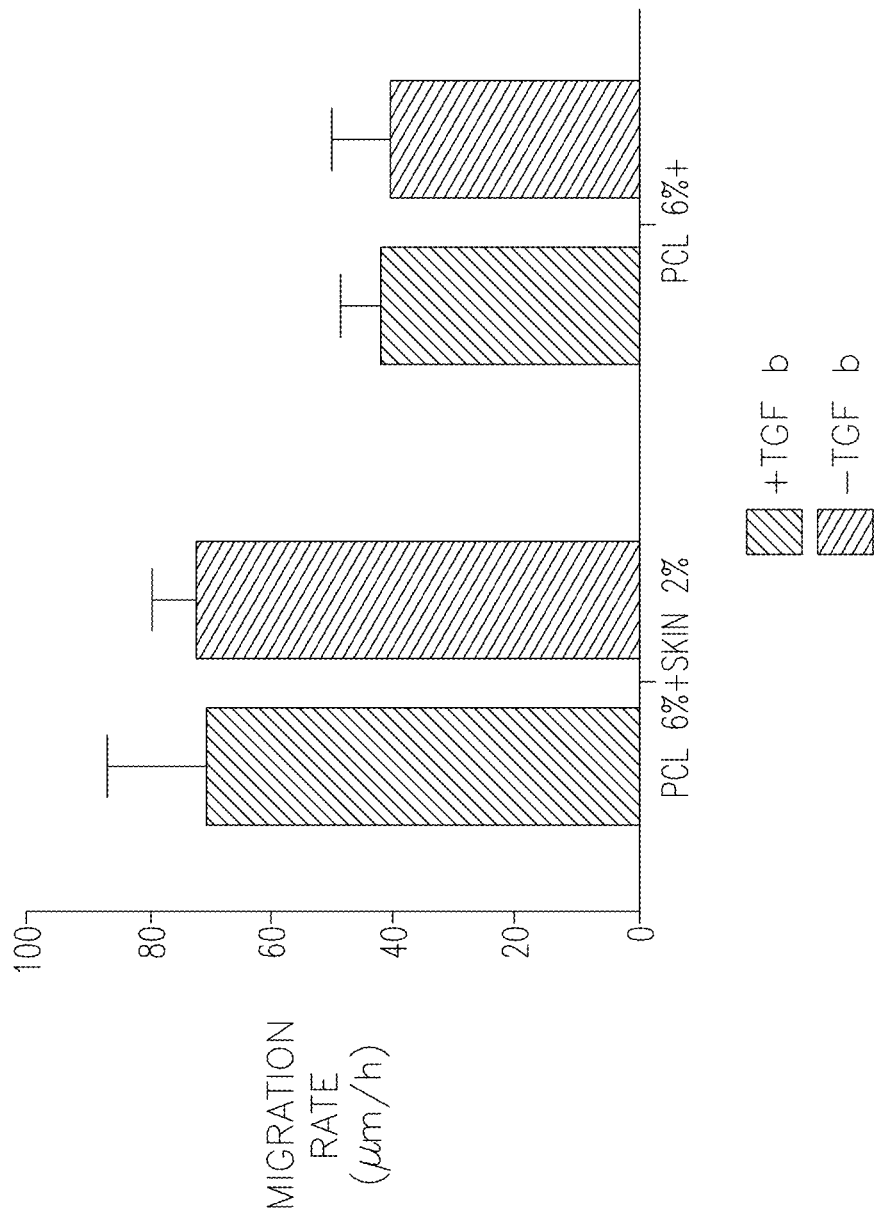
Figure 6E:
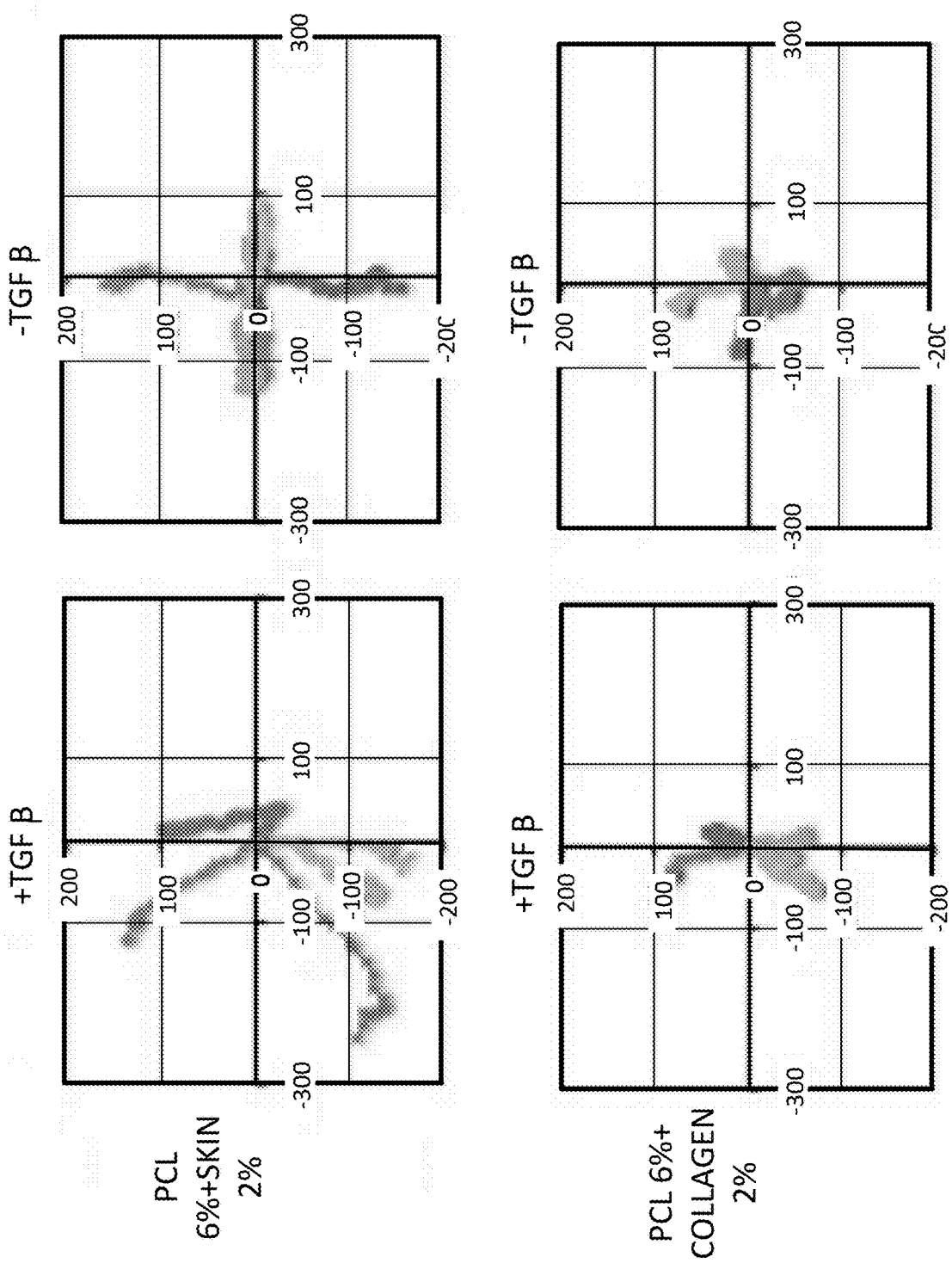
Figure 7:
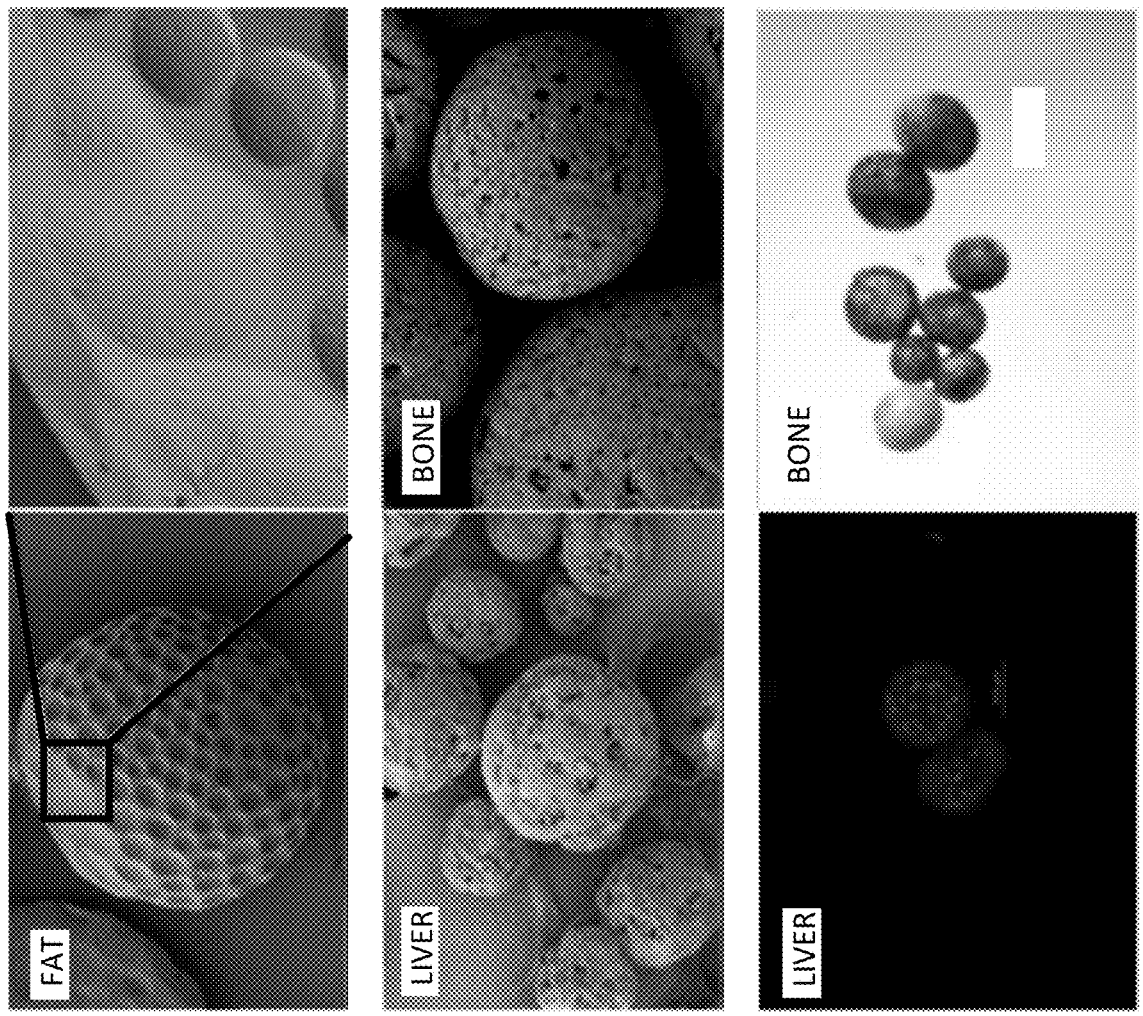
FIG. 7 shows representative scanning electron microscope (SEM) micrographs of the tissue-derived microbeads (top and middle panel) and cell attachment and growth on tissue-derived microbeads (bottom panel), wherein the cells were stained blue with methylene blue.

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign thereto.

Further, it should be noted that, as recited herein, the singular forms 'a,' "an," and "the" include the plural referents unless otherwise stated. Additionally, the terms "comprises" and "comprising" when used herein specify that certain features are present in that embodiment, however, this phrase should not be interpreted to preclude the presence of additional steps, operations, features, components, and/or groups thereof.

The present disclosure generally relates to a method for developing tissue-derived scaffolding materials in various formats. A main advantage of the tissue-derived scaffolding materials is that the materials mimic the ECM and therefore support the regeneration of different tissues, such as skin, bone, or cartilage.

A variety of scaffolding materials containing individual tissue matrix components in various formats such as fibers, sponges, films, particles/beads, depending on the application need, can be obtained by blending a homogenized tissue suspension with the corresponding solution composed of synthetic polymer (such as polycaprolactone (PCL), poly(lactic-co-glycolic acid) (PLGA)) or natural polymer (such as alginate, gelatin, collagen, chitosan), or a hybrid (such as PCL/collagen, PCL/chitosan) to form a homogeneous mixture. The mixture is then processed to form micro/nanofibers via extruding spinning/electrospinning, sponges via freeze-drying, films via casting and drying, particles/beads via extrusion/emulsion, hydrogel via gelation, and so on. These scaffolding materials are able to mimic ECM in two-dimensional (2D) or three-dimensional (3D) environments and, therefore, support the regeneration of different tissues, for example, skin, bone, or cartilage, and influence cancer cell proliferation and metastasis.

The tissue-derived suspension can be obtained through a series of processing procedures. In one embodiment, fresh tissues dissected from anatomical sites (such as animal or human) were first washed thoroughly with a sterile saline buffer, such as phosphate-buffered saline (PBS), at a low temperature (such as 4° C.), then frozen at −80° C. overnight (after an optional rinsing with deionized (DI) water), and subsequently lyophilized. Upon freeze-drying, a designated amount of tissues, which depends on the net weight of the tissue and varies from animal to animal, was mashed at a low temperature (for example, 4° C.), and then mixed with a specific solvent, such as hexafluoro-isopropanol (HFIP) or dichloromethylene (DCM), for homogenizing to form a tissue-derived suspension. A polymer solution of synthetic (such as PCL, PLGA) or natural (such as gelatin, collagen, chitosan) or hybrid (such as PCL/collagen, PCL/chitosan) was then mixed with the tissue-derived suspension at a certain ratio. Multiple ratios of PCL to tissue extract can be used, including, but not limited to 1:1, 1:2, 1:3, 1:4, 1:5 and so on. See Table 1 below for an exemplary formula for fabricating tissue-derived electrospun fiber matrices. The maximum tissue concentrations that were used are as follows:

Lung: 0.14 mg/mL
Liver: 2.64 mg/mL
Brain: 0.27 mg/mL
Bone: 1.27 mg/mL
Fat: 2.765 mg/mL.

TABLE 1

Representative formula for fabricating tissue-derived electrospun fiber matrices
The mixture was then further processed for fabrication into, for example, a porous sponge, fibrous matrices, microbeads, and films.

| Tissue Suspension + 8 (w/v) PCL | Tissue Concentration (mg/mL) | Voltage (kv)** |
|---|---|---|
| Lung | 46 | 9 |
| Liver | 44 | 11 |
| Brain | 90 | 9 |
| Bone | 11 | 17 |
| Fat | 922 | 9 |
| PCL (control) | 80 | 14 |

It has been observed that the preserved ECM molecules (such as collagen, proteoglycans) and regulatory molecules (such as growth factors) in the 3D scaffolds yield scaffolds with distinct chemical characteristics depending on the corresponding tissue-derived homogenized suspension being used, such as brain tissue, bone, lung, liver, and skin. Various types of cells have been cultured on these tissue-derived scaffolding materials so as to understand how the extracellular environment alters the phenotypic expression of cells. In one embodiment, human skin fibroblasts and cancer cells (breast cancer and melanoma) were respectively cultured on skin-derived fiber matrices, on liver, lung, bone, brain, and adipose-derived fiber matrices, and on nanofiber/tissue extract matrices. In another embodiment, breast cancer cells and endothelial cells were cultured on tissue-derived microbeads.

In yet another embodiment, it was shown that skin-derived fibrous matrices support wound-healing activities of human dermal fibroblasts. In this embodiment, skin tissue was homogenized within hexafluoro-isopropanol (HFIP) upon freeze-drying. The homogenized tissue suspension was mixed with the PCL/HFIP solution at a designated ratio, as explained previously. The mixture was then electropsun into fibrous matrices with either random, aligned, or patterned fiber organization. Wound healing behaviors of fibroblasts on such fibrous matrices were evaluated and it was found that skin-derived matrices promoted the migration and proliferation of fibroblasts in comparison to PCL/collagen nanofibers.

In another embodiment, it was shown that tissue-derived fibrous matrices differentially regulated breast cancer cells. In this embodiment, different tissues (bone, lung, liver, lymph and brain), upon freeze-drying, were homogenized in HFIP to obtain a respective tissue suspension. The suspension was then mixed with PCL/HFIP solution at a designated ratio, as explained previously. The mixture was then electropsun into fibrous matrices with either random, aligned, or patterned fiber organization. A culture of breast cancer cells (such as MCF-7 and MDA-MB-231 cells) on various tissue-derived matrices revealed that the metastatic phenotype of cancer cells was generally observed on the bone-derived matrices followed by lung or liver, lymph and then brain, consistent with clinical manifestation. The expression for E-cadherin and vimentin also showed significant differences between different tissue-derived matrices.

In another embodiment, it was shown that tissue-derived fibrous matrices differentially regulated melanoma cancer cells. In this embodiment, different tissues (bone, lung, liver, lymph and brain), upon freeze-drying, were homogenized in HFIP to obtain a respective tissue suspension. The suspension was then mixed with PCL/HFIP solution at a designated ratio, as explained previously. The mixture was then electropsun into fibrous matrices with either random, aligned, or patterned fiber organization. A culture of human melanoma cancer cells (C 8161.9 cells and KFM 8161.9 cells) on various tissue-derived matrices suggested that both cells migrated, however, the cultures showed significant migratory capacity on brain-derived fibrous matrices, while much less so on the bone-derived matrices. Meanwhile, only the C8161 cells proliferated more on the brain-derived matrices. E-cadherin expression on different matrices varied as well and C8161 expressed more on the lung-derived matrices.

In another embodiment, it was shown that tissue-derived microbeads support 3D tissue formation. In this embodiment, different tissues, upon freeze-drying, were homogenized in dichloromethylene (DCM) to obtain a respective tissue suspension. The suspension was then mixed with a PCL/DCM solution at a designated ratio, as explained previously. In particular, the ratio of liver or bone tissue extract and polymer solution can vary from 1:1 to 1:3. The ratio of fat tissue extract and polymer solution can vary from 1:2 to 1:4. The mixture was used to fabricate microbeads through the water-oil emulsion method. Microbeads exhibited different surface properties for different tissue suspensions such as liver, fat, and bone. For example, shallow small pores were seen with fat-derived microbeads, possibly caused by oil droplets of fat tissue. Both liver and bone-derived microbeads somehow showed a very rough surface with small pores. A culture of breast cancer cells and endothelial cells on these microbeads revealed that fat-derived microbeads did not support the attachment of both cells due to their highly hydrophobic surface, while the liver and bone-derived microbeads favored cell attachment.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It will be understood that the embodiments described herein are merely exemplary and that a person skilled in the art may make many variations and modifications without departing from the spirit and scope of the invention. All such variations and modifications are intended to be included within the scope of the invention.

We claim:

1. A method of making tissue-derived scaffolding materials, consisting of the steps of:
    obtaining fresh tissue from an anatomical site;
    washing the tissue with a sterile saline buffer at a low temperature to preserve extracellular matrix molecules in the tissue;
    freezing the washed tissue;
    lyophilizing the frozen tissue;
    mashing the lyophilized tissue at a low temperature;
    adding a solvent to the mashed tissue to form a tissue/solvent mixture;
homogenizing the tissue/solvent mixture to form a tissue-derived suspension; and
    mixing the tissue-derived suspension with a polymeric solution to obtain a homogeneous mixture for producing the tissue-derived scaffolding materials.

2. The method of claim 1, wherein the tissue-derived scaffolding materials are a three-dimensional scaffold material.

3. The method of claim 2, wherein the three-dimensional scaffold material is in the form of a sponge.

4. The method of claim 2, wherein the three-dimensional scaffold material is in the form of a hydrogel.

5. The method of claim 2, wherein the three-dimensional scaffold material is in the form of a film.

6. The method of claim 2, wherein the three-dimensional scaffold material is in the form of a fiber or fibers.

7. The method of claim 2, wherein the three-dimensional scaffold material is in the form of a particle or particles.

8. The method of claim 2, wherein the three-dimensional scaffold material is in the form of a bead or beads.

9. The method of claim 1, wherein the fresh tissue is obtained from an autogenic human source.

10. The method of claim 1, wherein the washing step is carried out at a temperature of 4° C.

11. The method of claim 1, wherein the mashing step is carried out at a temperature of 4° C.

12. The method of claim 1, wherein the solvent is hexafluoro-isopropanal.

13. The method of claim 1, wherein the solvent is dichloromethylene.

14. The method of claim 1, wherein the polymeric solution is a synthetic polymer.

15. The method of claim 1, wherein the polymeric solution is a natural polymer.

16. The method of claim 1, wherein the polymeric solution is a synthetic/natural hybrid polymer.

17. The method of claim 1, wherein the freezing step is carried out at a temperature of −80° C.

* * * * *